United States Patent
Tang et al.

(10) Patent No.: US 9,125,590 B2
(45) Date of Patent: Sep. 8, 2015

(54) MEDICAL VENTILATOR CAPABLE OF EARLY DETECTING AND RECOGNIZING TYPES OF PNEUMONIA, GAS RECOGNITION CHIP, AND METHOD FOR RECOGNIZING GAS THEREOF

(75) Inventors: Kea-Tiong Tang, Taipei (TW); Chung-Hung Shih, Taipei (TW); Li-Chun Wang, Longtan Township (TW); Hsin Chen, Yilan (TW); Yi-Wen Liu, Hsinchu (TW); Jyuo-Min Shyu, Hsinchu (TW); Chia-Min Yang, Hsinchu (TW); Da-Jeng Yao, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 669 days.

(21) Appl. No.: 13/458,533

(22) Filed: Apr. 27, 2012

(65) Prior Publication Data

US 2013/0197384 A1    Aug. 1, 2013

(30) Foreign Application Priority Data

Feb. 1, 2012   (TW) .............................. 101103310 A

(51) Int. Cl.
*A61B 5/08* (2006.01)
*G01N 33/497* (2006.01)
(Continued)

(52) U.S. Cl.
CPC ............... *A61B 5/082* (2013.01); *A61B 5/7264* (2013.01); *G01N 33/497* (2013.01); *G01N 2033/4975* (2013.01); *G06K 9/00* (2013.01)

(58) Field of Classification Search
CPC ........ A61B 5/082; A61B 5/72; A61B 5/7257; A61B 5/726; G01N 33/497; G01N 2001/2244; A61M 2230/43
See application file for complete search history.

(56) References Cited

U.S. PATENT DOCUMENTS 4,945,257 A * 7/1990 Marrocco, III ................. 338/38
5,412,256 A * 5/1995 Alspector et al. ............... 706/38
(Continued)

FOREIGN PATENT DOCUMENTS

CN    1647756 A    8/2005

OTHER PUBLICATIONS

Keller, Paul E. "Electronic noses and their applications." Northcon 95. I EEE Technical Applications Conference and Workshops Northcon95. IEEE, 1995.*

(Continued)

*Primary Examiner* — Lisa Caputo
*Assistant Examiner* — Punam Roy
(74) *Attorney, Agent, or Firm* — Wang Law Firm, Inc.; Li K. Wang; Stephen Hsu

(57) ABSTRACT

A medical ventilator capable of early detecting and recognizing types of pneumonia, a gas recognition chip, and a method for recognizing gas thereof are disclosed. The gas recognition chip of the medical ventilator comprises a sensor array, a sensor interface circuit, a stochastic neural network chip, a memory and a microcontroller. The sensor array receives a plurality of multiple types of gases to produce odor signals corresponding to each type of gas. The sensor interface circuit analyzes the odor signals to produce gas pattern signals corresponding to each type of gas. The stochastic neural network chip amplifies the differences between the gas pattern signals and performs dimensional reduction on the gas pattern signals to aid the analysis. The memory stores training data. The microcontroller performs a mixed gas recognizing algorithm to early detect and recognize the type of the pneumonia according to the gas training data.

14 Claims, 12 Drawing Sheets

(51) Int. Cl.
*A61B 5/00* (2006.01)
*G06K 9/00* (2006.01)

(56) References Cited

U.S. PATENT DOCUMENTS

| | | | | |
|---|---|---|---|---|
| 6,759,010 | B2* | 7/2004 | Lewis et al. | 422/82.02 |
| 7,122,152 | B2* | 10/2006 | Lewis et al. | 422/50 |
| 7,462,512 | B2* | 12/2008 | Levon et al. | 438/123 |
| 8,801,610 | B2* | 8/2014 | Brauker et al. | 600/365 |
| 2002/0151814 | A1* | 10/2002 | Payne et al. | 600/532 |
| 2003/0186461 | A1* | 10/2003 | Boehr et al. | 436/181 |
| 2007/0089516 | A1* | 4/2007 | Khuri-Yakub et al. | 73/579 |
| 2007/0167853 | A1* | 7/2007 | Melker et al. | 600/532 |
| 2009/0261987 | A1* | 10/2009 | Sun | 340/870.07 |
| 2010/0086933 | A1* | 4/2010 | Hospach et al. | 435/6 |
| 2010/0137733 | A1* | 6/2010 | Wang et al. | 600/532 |
| 2010/0288014 | A1* | 11/2010 | Yao et al. | 73/24.06 |
| 2012/0183949 | A1* | 7/2012 | Hyde et al. | 435/5 |
| 2012/0326092 | A1* | 12/2012 | Haick et al. | 252/408.1 |
| 2013/0064423 | A1* | 3/2013 | Joseph et al. | 382/103 |
| 2013/0122191 | A1* | 5/2013 | Wang et al. | 427/122 |
| 2013/0150261 | A1* | 6/2013 | Haick et al. | 506/12 |
| 2013/0152349 | A1* | 6/2013 | Wang et al. | 29/25.01 |
| 2013/0304395 | A1* | 11/2013 | Naidu et al. | 702/25 |

OTHER PUBLICATIONS

Snopok, B. A., and I. V. Kruglenko. "Multisensor systems for chemical analysis: state-of-the-art in electronic nose technology and new trends in machine olfaction." Thin Solid Films 418.1 (2002): 21-41.*
Tang, Kea-Tiong, et al. "A low-power electronic nose signal-processing chip for a portable artificial olfaction system." Biomedical Circuits and Systems, IEEE Transactions on 5.4 (Apr. 5, 2011): 380-390.*
Tang, Tong Boon, and Alan F. Murray. "Multisensor Fusion for Low-Power Wireless Microsystems." Perception-Action Cycle. Springer Series in Cognitive and Neural Systems, 711-748. Chapter online publication date: Dec. 31, 2010. Acessed online at <http://link.springer.com/chapter/10.1007%2F978-1-4419-1452-1_22>.*
"Special Electronic Nose System for Agriculture Products Quality Detection", see Abstract.
"Experimental Study on SAW SO2 Sensor Based on Carbon Nanotube-polyanilin Films", see Abstract.
English translation of Office Action of corresponding CN application published Nov. 18, 2013.
C. C. Lu and H. Chen; "Current-mode Computation with Noise in a Scalable and Programmable Probabilistic Neural VLSI System", Artificial Neural Networks-ICANN 2009. Springer Berlin Heidelberg, 2009. pp. 401-409.

* cited by examiner

MEDICAL VENTILATOR CAPABLE OF EARLY DETECTING AND RECOGNIZING TYPES OF PNEUMONIA, GAS RECOGNITION CHIP, AND METHOD FOR RECOGNIZING GAS THEREOF

CROSS-REFERENCE TO RELATED APPLICATION

This application claims the benefit of Taiwan Patent Application No. 101103310, filed on Feb. 1, 2012, in the Taiwan Intellectual Property Office, the disclosure of which is incorporated herein in its entirety by reference.

BACKGROUND OF THE INVENTION

1. Field of the Invention

The present invention relates to an electronic device used for recognizing a gas, more particularly to a medical ventilator having a micro gas recognition chip capable of recognizing the type of a mixed gas to early detect and recognize the types of pneumonia that infects a patient.

2. Description of the Related Art

After patients with severe illness enter into an intensive unit, the patients usually require intubations and medical ventilators, and thus the patients' respiratory tract may be infected easily to cause pneumonia, and the chance of getting pneumonia in this situation may reach 80%. Many bacteria causing pneumonia already have drug resistance, and thus making the treatment more difficult.

If a patient has the symptoms of pneumonia, medical professionals will take X-ray photo of the patient's chest, blood samples and phlegm suction to perform a bacterial culture of molecular biology. However, even if medical professionals have confirmed that a patient is infected by pneumonia from blood extraction, phlegm suction and chest X-ray examination, it is necessary to wait for the result of the bacterial culture to conform the bacteria causing the pneumonia, and the bacterial culture generally takes at least five days which is a very long time to the critically ill patient. At present, there is no medical instrument available for diagnosing the patient's types of pneumonia immediately, and doctors usually require giving mediations to the patient before the result of the bacterial culture is obtained. However, at least ten types of bacteria (such as *pseudomonas aeruginosa, Klebsiella pneumoniae, acinetobacter baumannii* and *staphylococcus*, etc) will cause pneumonia, and the medicines used for treating different types of bacteria are different. Therefore, the doctors can only based on experience to determine to use which medicine before the result of the bacterial culture is obtained. If the medicine is found to be inappropriate after the result of the bacterial culture is obtained, then the medicine is changed to another one. However, such delay of medical treatment will extend the patient's stay in the intensive care unit and increase the probability of the patient's nosocomial infection or even death. Therefore, it is an important subject for the present invention to provide an electronic device capable of diagnosing the types of pneumonia infecting the patient immediately.

SUMMARY OF THE INVENTION

In view of the shortcomings of the prior art, it is a primary objective of the present invention to overcome the aforementioned drawbacks of the prior art by providing a medical ventilator capable of early detecting and recognizing the types of pneumonia, a gas recognition chip, and a method for recognizing gas thereof to overcome the problem of the conventional medical testing system that cannot detect the types of pneumonia infecting a patient.

To achieve the aforementioned objective, the present invention provides a gas recognition chip, comprising: a sensor array, including a plurality of sensors and a sensing film, wherein the sensing film adsorbs plural types of gases, and each of the sensors produces an odor signal corresponding to each of the respective gases; a sensor interface circuit, for reading and analyzing the odor signal of each of the gases to generate a gas pattern signal corresponding to each of the respective gases; a stochastic neural network chip, for amplifying the difference between the gas pattern signals and reducing the dimensions of each gas pattern signal to assist producing an analysis result; a memory, for storing gas training data; and a microcontroller, for receiving the analysis result, executing a mixed gas recognizing algorithm according to the analysis result to recognize the type of the gas, classifying an unknown gas not existed in the gas training data, and producing a recognition result according to the gas training data.

To achieve the aforementioned objective, the present invention further provides a method for recognizing gas, and the method comprises the steps of: using a sensing film of a sensor array to adsorb plural types of gases, such that each sensor of the sensor array generates an odor signal corresponding to each of the respective gases; using a sensor interface circuit to read and analyze the odor signal of each of the gases to generate a gas pattern signal corresponding to each of the respective gases; using a stochastic neural network chip to amplify the difference between the gas pattern signals and reduce the dimensions of each of the gas pattern signals to produce an analysis result; storing gas training data in a memory; and using a microcontroller to receive the analysis result, and execute a mixed gas recognizing algorithm to identify the type of the gas according to the analysis result, and classify an unknown gas not existed in the gas training data, and then produce a recognition result according to the gas training data.

Preferably, the sensing film is made of a nanoporous carbon material. A polymer with gas adsorbability is grown in pores of the nanoporous carbon material.

Preferably, when the microcontroller detects the unknown gas, the microcontroller transmits data of the unknown gas to the sensor interface circuit, the stochastic neural network chip and the memory, so that the gas recognition chip has a self-learning ability.

Preferably, the mixed gas recognizing algorithm includes a K nearest neighbor (KNN) algorithm, a linear least squares regression algorithm and a median-threshold K nearest neighbor (MTKNN) classification algorithm. The median-threshold K nearest neighbor classification algorithm is used to find a distance between every two data in the gas training data, and then find a median of the distances. The median is used to determine whether the gas is the unknown gas.

Preferably, the sensor array is comprised of conducting polymer (CP) sensors.

Preferably, the sensor interface circuit stores electric charges by a single polysilicon floating gate element to reduce electric leakage and circuit power.

Preferably, the sensor array is comprised of surface acoustic wave (SAW) sensors.

Preferably, the sensor interface circuit includes an adjustable oscillator circuit for adjusting an oscillation frequency by different surface acoustic wave sensors to enhance the flexibility of usage.

To achieve the aforementioned objective, the present invention further provides a medical ventilator capable of early detecting and recognizing types of pneumonia, and the medical ventilator comprises an aspiration pipeline and a gas recognizing device, and the gas recognizing device uses the aforementioned gas recognition chip to analyze a gas aspired by a patient from the aspiration pipeline to identify the type of pneumonia.

Preferably, the gas recognizing device is coupled directly to the aspiration pipeline outside the patient's body, and the gas aspired by the patient is collected to perform a recognition.

In summation, the medical ventilator capable of early detecting and recognizing types of pneumonia, the gas recognition chip and the method for recognizing gas thereof in accordance with the present invention have one or more of the following advantages:

(1) The gas recognition chip of the present invention uses the nanoporous carbon material to form the sensing film and grows a polymer with gas adsorbability in pores of the nanoporous carbon material, so that the sensitivity of detecting the gas, the selectivity of gases, and the detection limit can be enhanced.

(2) The gas recognition chip of the medical ventilator capable of early detecting and recognizing types of pneumonia of the present invention adopts a stochastic neural network chip for the pretreatment of the gas pattern signal, so as to improve the recognition precision significantly and reduce the computation and power of the system.

(3) The gas recognition chip of the medical ventilator capable of early detecting and recognizing types of pneumonia of the present invention adopts an algorithm with robustness and adaption to recognize a mixed gas and classify an unknown gas effectively.

(4) The sensor interface circuit of the gas recognition chip of the medical ventilator capable of early detecting and recognizing types of pneumonia of the present invention adopts a single polysilicon floating gate element to store electric charges, so as to reduce electric leakage and circuit power.

(5) The sensor interface circuit of the gas recognition chip of the medical ventilator capable of early detecting and recognizing types of pneumonia of the present invention further comprises an adjustable oscillator circuit that can adjust an oscillation frequency according to different surface acoustic wave sensors, so as to improve the flexibility of usage.

(6) The gas recognition chip of the present invention can be implemented by a system on chip, so as to reduce the volume of the gas recognizing device significantly and integrate the chip with the medical ventilator to instantly detect the types of pneumonia of each patient and assist doctors to make correct diagnosis. The gas recognition chip can be applied on other portable electronic devices to execute different functions.

DETAILED DESCRIPTION OF THE PREFERRED EMBODIMENTS

Figure 1:
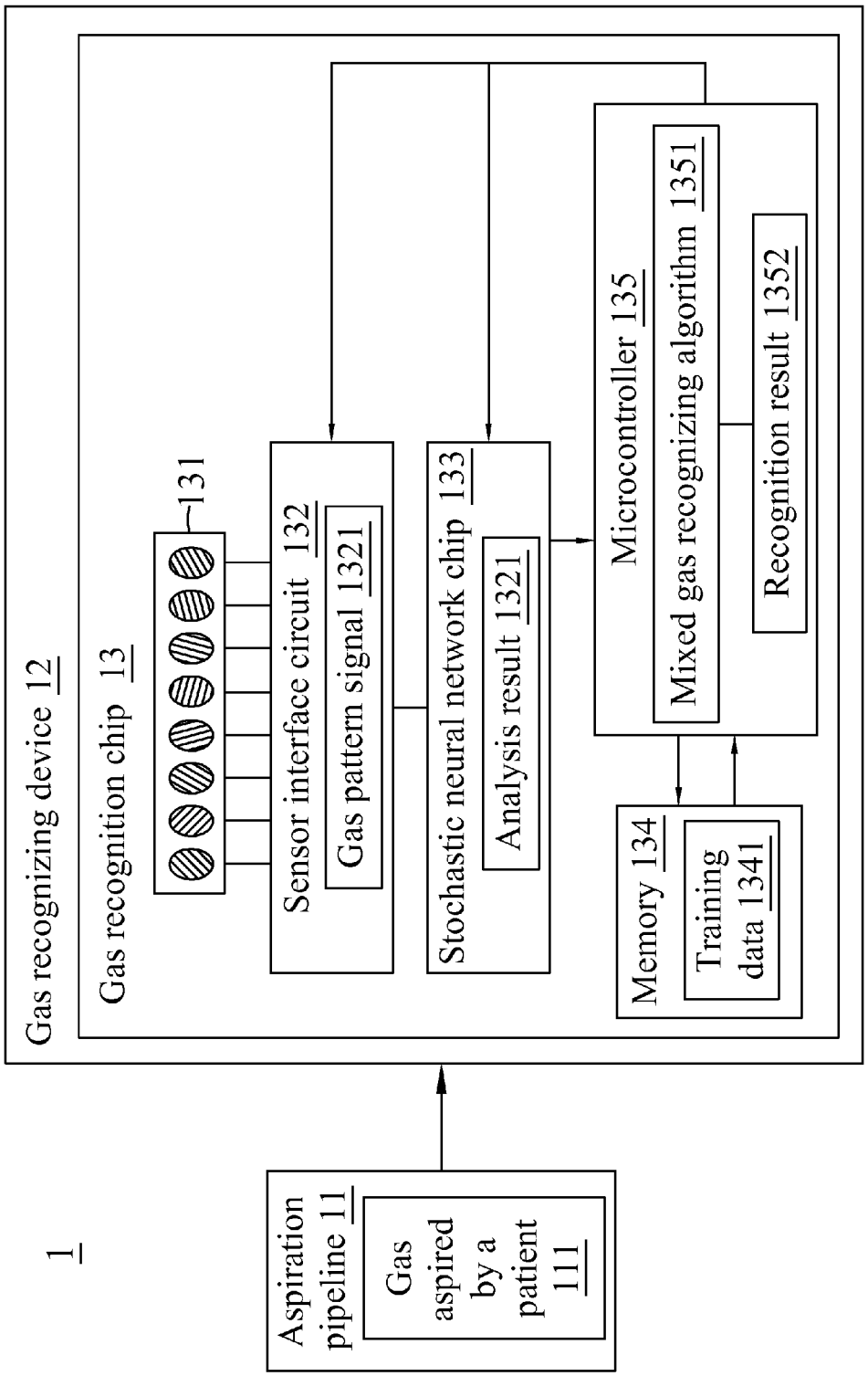
FIG. 1 is a block diagram of a medical ventilator for early detecting and recognizing types of pneumonia in accordance with the present invention.

The technical characteristics of the present invention will become apparent with the detailed description of the preferred embodiments accompanied with the illustration of related drawings as follows. It is noteworthy to point out that same numerals are used for representing the same respective elements in the drawings.

With reference to FIG. 1 for a block diagram of a medical ventilator for early detecting and recognizing types of pneumonia in accordance with the present invention, the medical ventilator 1 comprises an aspiration pipeline 11 and a gas recognizing device 12. The gas recognizing device 12 uses a gas recognition chip 13 to analyze a mixed gas 111 aspired by a patient through the aspiration pipeline 11 to recognize the types of pneumonia of the patient. The gas recognition chip 13 comprises a sensor array 131, a sensor interface circuit 132, a stochastic neural network chip 133, a memory 134 and a microcontroller 135. The microcontroller 135 is coupled to the sensor interface circuit 132, the stochastic neural network chip 133 and the memory 134 to control their operation.

The sensor array 131 comprises a plurality of sensors and a sensing film, and the sensing film can adsorb a mixed gas 111 aspired by a patient from plural types of gases, and each sensor in the sensor array 131 is used for generating an odor signal corresponding to each type of gas.

Preferably, the sensing film is made of the nanoporous carbon material, and a polymer with gas adsorbability is grown in pores of the nanoporous carbon material, and different types of polymer materials are selected for composing a variety of nano composite materials with high-density functional groups. The sensing film produce by this method can improve the sensitivity of detecting the gas, the selectivity of gases, and the detection limit. Wherein, the sensor array includes conducting polymer (CP) sensors or surface acoustic wave (SAW) sensors.

The sensor interface circuit 132 reads and analyzes the odor signal transmitted from the sensor array to generate a gas pattern signal 1321 corresponding to each type of gas. Wherein, the sensor array 131 can generate the gas pattern signal 1321 corresponding to each type of gas through the whole reaction of the mixed gas of the whole array, and the sensor interface circuit 132 is used for generating the gas pattern signal 1321 corresponding to each type of gas. The stochastic neural network chip 133 amplifies the differences between gas pattern signals 1321 and reduces the dimensions of each gas pattern signal 1321 to produce an analysis result 1331.

In addition, the stochastic neural network chip 133 can capture the main characteristics of the signals by using a learning algorithm, so as to provide an output with dimension lower than that of the original signal to reduce the computation of a backend system.

The memory 134 stores training data 1341, wherein the training data 1341 includes gas data generated from various types of bacteria causing pneumonia and other possible gas data. The microcontroller 135 receives the analysis result 1331, executes a mixed gas recognizing algorithm 1351 to recognize the type of gas according to the analysis result 1331, classifies an unknown gas, which is not existed in the training data 1341, and produces a recognition result 1352 according to the training data 1341.

Further, if the microcontroller 135 detects an unknown gas not existed in the training data 1341, the microcontroller 135 will classify the unknown gas and transmit the data of the unknown gas to the sensor interface circuit 132, the stochastic neural network chip 133 and the memory 134. Therefore, the sensor interface circuit 132 can perform the recognition according to the data of the unknown gas, the stochastic neural network chip 133 can perform the training according to the data of the unknown gas, and the type of the training data 1341 of the memory 134 can be added.

It is noteworthy that metabolites will be produced while the bacteria causing pneumonia are growing, and these metabolites include gases. The gases produced by the metabolites of different bacteria are different, and a ward of a hospital may contain other gases irrelevant to pneumonia. Therefore, the microcontroller 135 has to execute the mixed gas algorithm to recognize the gas which is the gas produced by the bacteria causing pneumonia or the gas irrelevant to pneumonia, and then compares the gas with the training data 1341 to recognize the type of pneumonia that affects the patient. If the mixed gas detected by the mixed gas algorithm of the present invention includes an unknown gas, each known composition of the mixed gas still can be recognized effectively. If the unknown gas occurs frequently, the microcontroller 135 can automatically determine and classify the unknown gas into a new type. Therefore, the gas recognition chip 13 of the present invention has the features of robustness and adaption.

Preferably, the mixed gas algorithm of the present invention includes a K nearest neighbor (KNN) algorithm, a linear least squares regression algorithm and a median-threshold K nearest neighbor (MTKNN) classification algorithm.

The K nearest neighbor algorithm can be used for classify the gas signal preliminarily, and the algorithm recognizes the type of gas by the similarity of the gas data between gas reaction signals and the training data 1341. If the difference of all data between the gas and the training data 1341 is greater than a critical point, then the system will classify this unknown gas as a new gas and store the new gas in the training data. The K nearest neighbor algorithm can classify the gas into the most similar training data in order to learn about the similarity of a mixed gas with different compositions, and then the position of the mixed gas is used to find a pure gas nearby in order to determine the composition of this mixed gas. The linear least squares regression algorithm can be used for estimating the concentration of each composition of the mixed gas.

Figure 2:
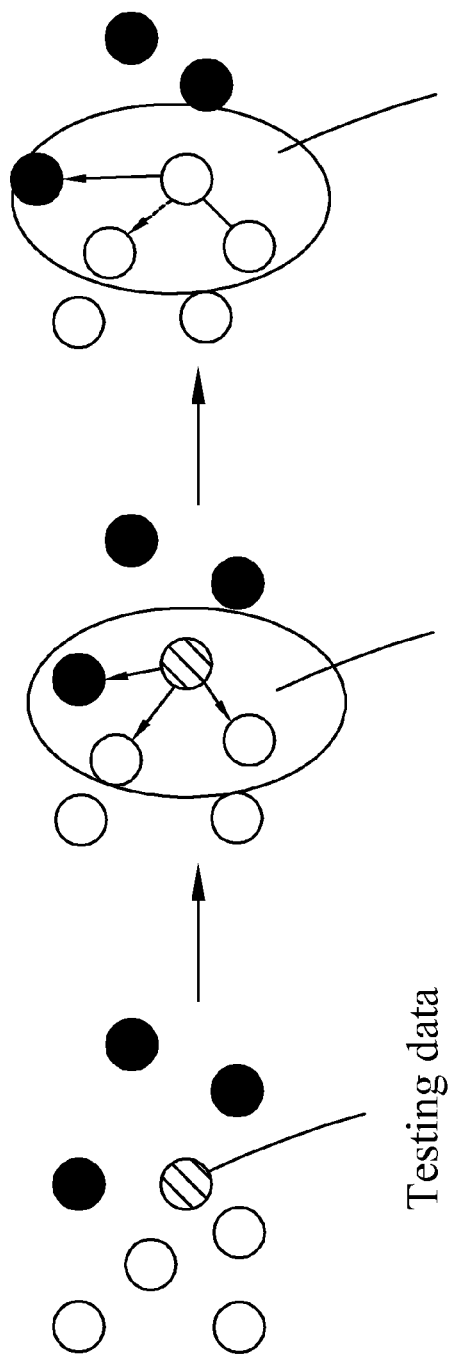
FIG. 2 is a schematic view of a gas recognition chip that adopts a median-threshold K nearest neighbor (MTKNN) classification algorithm in accordance with the present invention.

With reference to FIG. 2 for a schematic view of a gas recognition chip that adopts a median-threshold K nearest neighbor (MTKNN) classification algorithm in accordance with the present invention, the gas recognition chip 13 must have an effective elimination mechanism to avoid misjudgments in order to effectively classify the unknown gas. The present invention provides a novel median-threshold K nearest neighbor classification algorithm to determine whether or not the gas is an unknown gas. In the median-threshold K nearest neighbor classification algorithm, distances between every two training data of each type in the training data are found first, and then a median of the distances is calculated and used as a critical value. During the process of recognizing the gas, the K nearest neighbor algorithm is used to find K neighbors closest to this gas, and the median of the distances between the gas and the K neighbors is calculated. This median must be smaller than the critical value. If the median is greater than the critical value, the gas is considered as an unknown gas.

In FIG. 2, a classification procedure with K=3 and class=2 is demonstrated. Firstly, the distances between a testing data and all training data are calculated. Since K=3, it is necessary to find three neighbors closest to the testing data. There are two of the three neighbors of the testing data falling into the white class, so that the testing data is determined and classified as white class. In addition, the median (indicated by the dotted-line arrow in the figure) of the distances between the testing data and the three neighbors must be smaller than the critical value of the white class.

Therefore, the mixed gas recognizing algorithm of the present invention integrates the median-threshold K nearest neighbor classification algorithm, not just capable of detecting the composition of the known gas in the mixed gas accurately, but also capable of determining the composition of the unknown gas in the mixed gas and classifying the unknown gas. Obviously, the mixed gas algorithm of the present invention has the features of robustness and adaption.

Figure 3A:
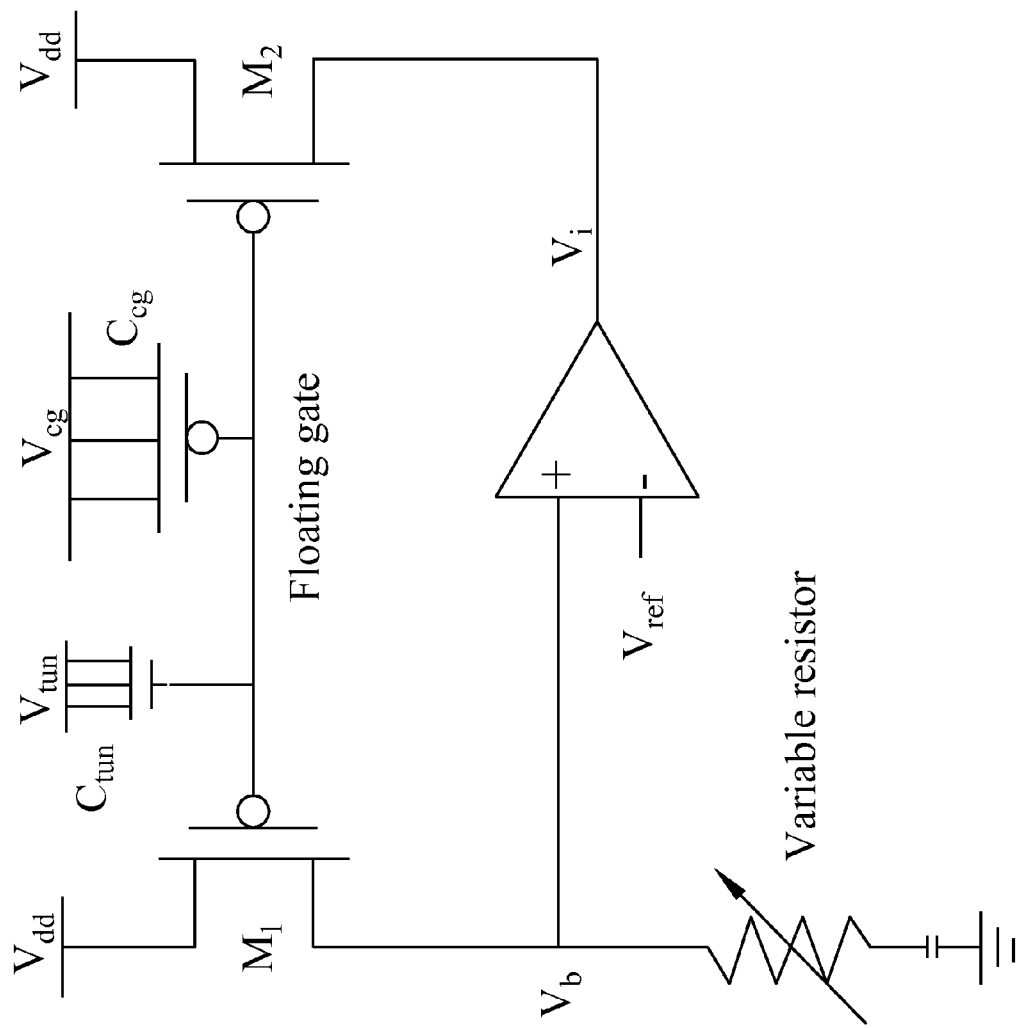
FIG. 3A is a circuit diagram of a conducting polymer sensor interface of a gas recognition chip in accordance with a preferred embodiment of the present invention.
Figure 3B:
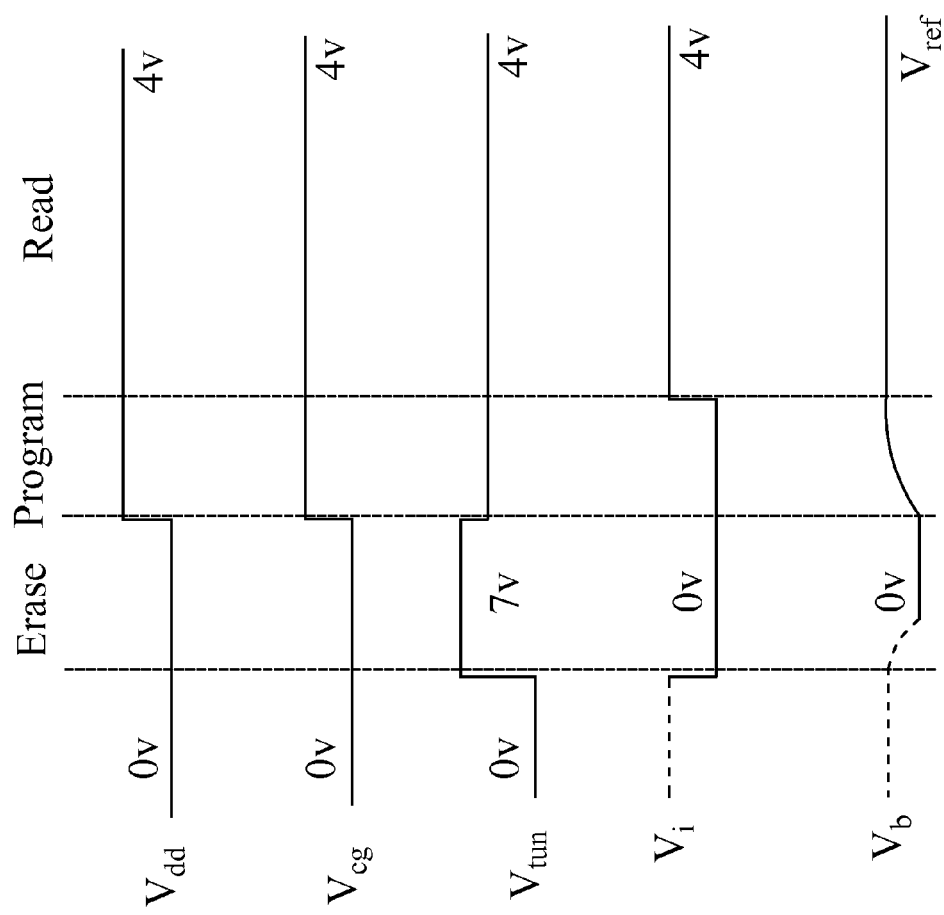
FIG. 3B shows the operation of a conducting polymer sensor interface of a gas recognition chip in accordance with a preferred embodiment of the present invention.
Figure 3C:
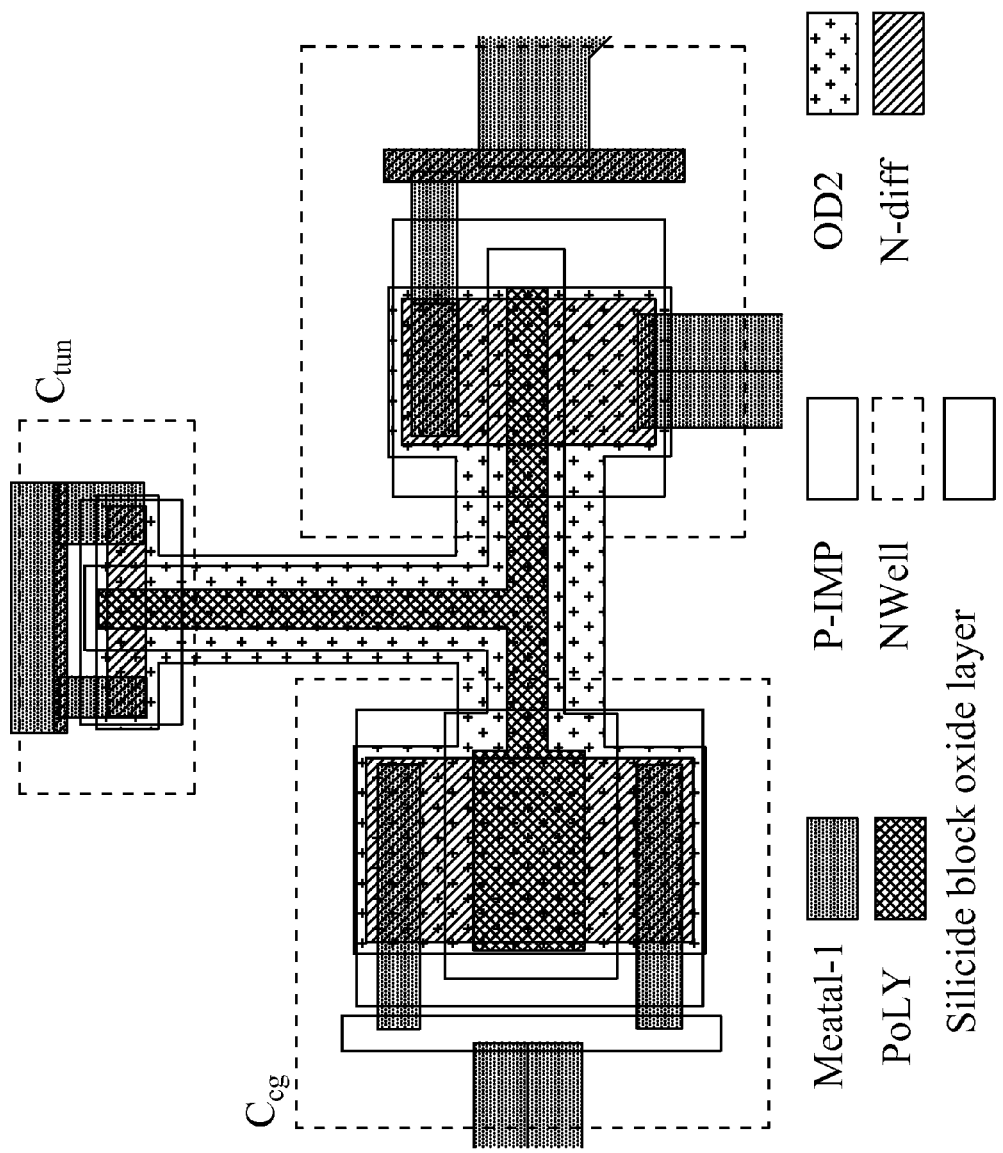
FIG. 3C shows a floating gate element of a conducting polymer sensor interface of a gas recognition chip in accordance with a preferred embodiment of the present invention.

With reference to FIGS. 3A, 3B and 3C for a circuit diagram of a conducting polymer sensor interface of a gas recognition chip in accordance with a preferred embodiment of the present invention, a schematic view of the operation of a conducting polymer sensor interface of the gas recognition chip in accordance with a preferred embodiment of the present invention, and a schematic view of a floating gate element of the conducting polymer sensor interface of the gas recognition chip in accordance with a preferred embodiment of the present invention respectively, a sensor array 131 of the present invention comprises a conducting polymer sensor. In FIG. 3A, the present invention replaces the capacitor and resistor used for storing electric charges by a single polysilicon floating gate element, so that a conducting polymer sensor interface circuit comprised of only two transistors, an amplifier and a floating gate element. The conducting polymer sensor interface circuit can be used to achieve low power consumption and overcome the serious electric leakage problem of the conventional analog method. The operation of the circuits is shown in FIG. 3B.

FIG. 3C shows a schematic view of a floating gate element in accordance with a preferred embodiment of the present invention. The floating gate element has a control gate which is a field effect transistor (FET) capacitor $C_{cg}$ for connecting the source, drain and body of a PMOS. Electric charges on a channel and the floating gate element are coupled at this terminal. An OD2 mask is used for increasing the thickness (approximately 7 nm) of silicon oxide to improve the data retention of the devices. Preferably, the PMOS can be used as a working transistor, so that the read operation can be completed with a smaller working current, so as to reduce the power consumption and achieve a higher reliability of the devices. A transistor $C_{tun}$ can be used to erase electrons on the floating gate device. The transistor manufactured with a smaller size can achieve a smaller coupling ratio to improve the erase efficiency. In the figure, Metal-1 stands for a metal layer, P-IMP stands for a P-type ion implant, OD2 stands for a thick oxide layer, and Poly stands for polysilicon.

Figure 4A:
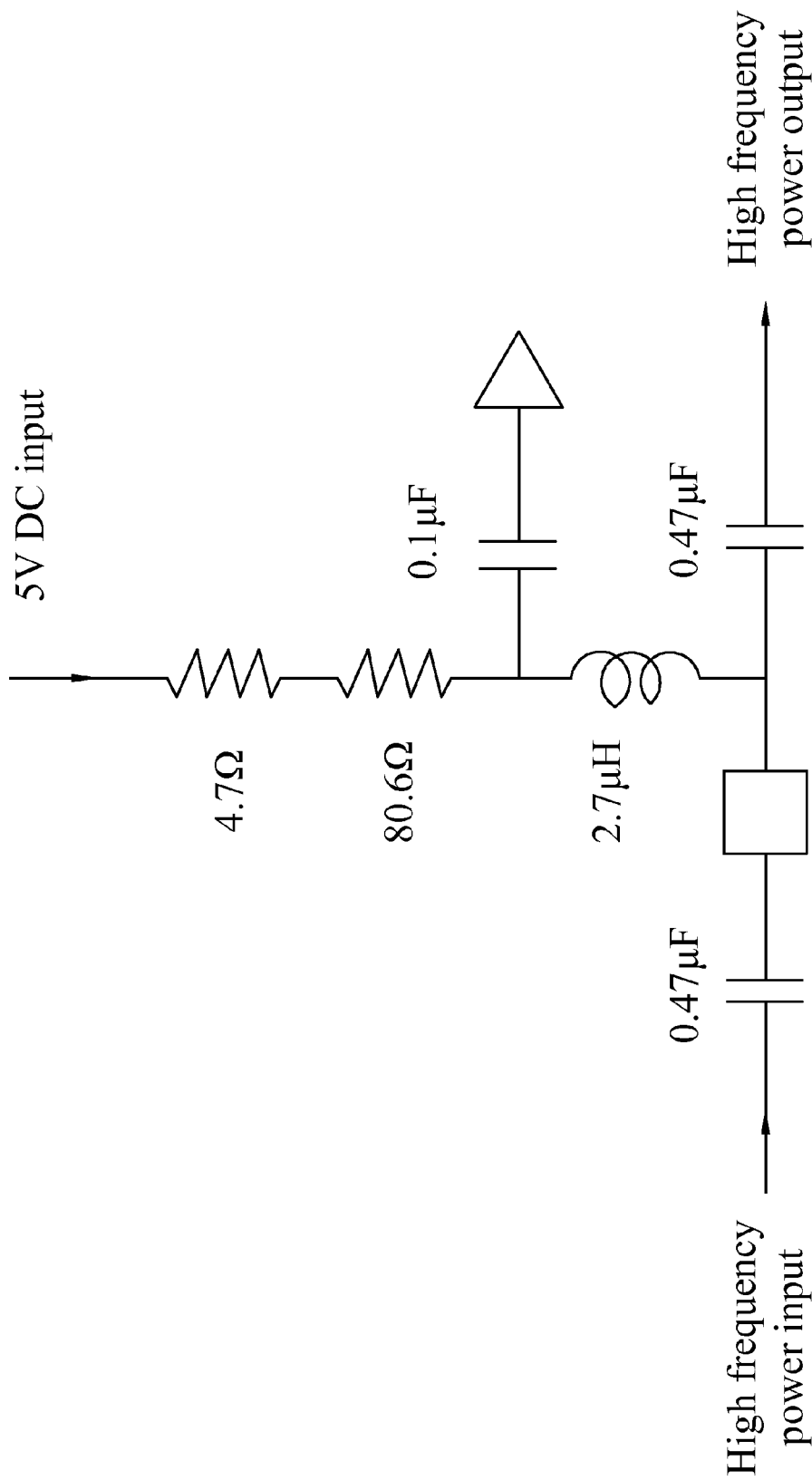
FIG. 4A is a circuit diagram of an adjustable oscillator circuit of a surface acoustic wave sensor interface circuit of a gas recognition chip in accordance with a preferred embodiment of the present invention.
Figure 4B:
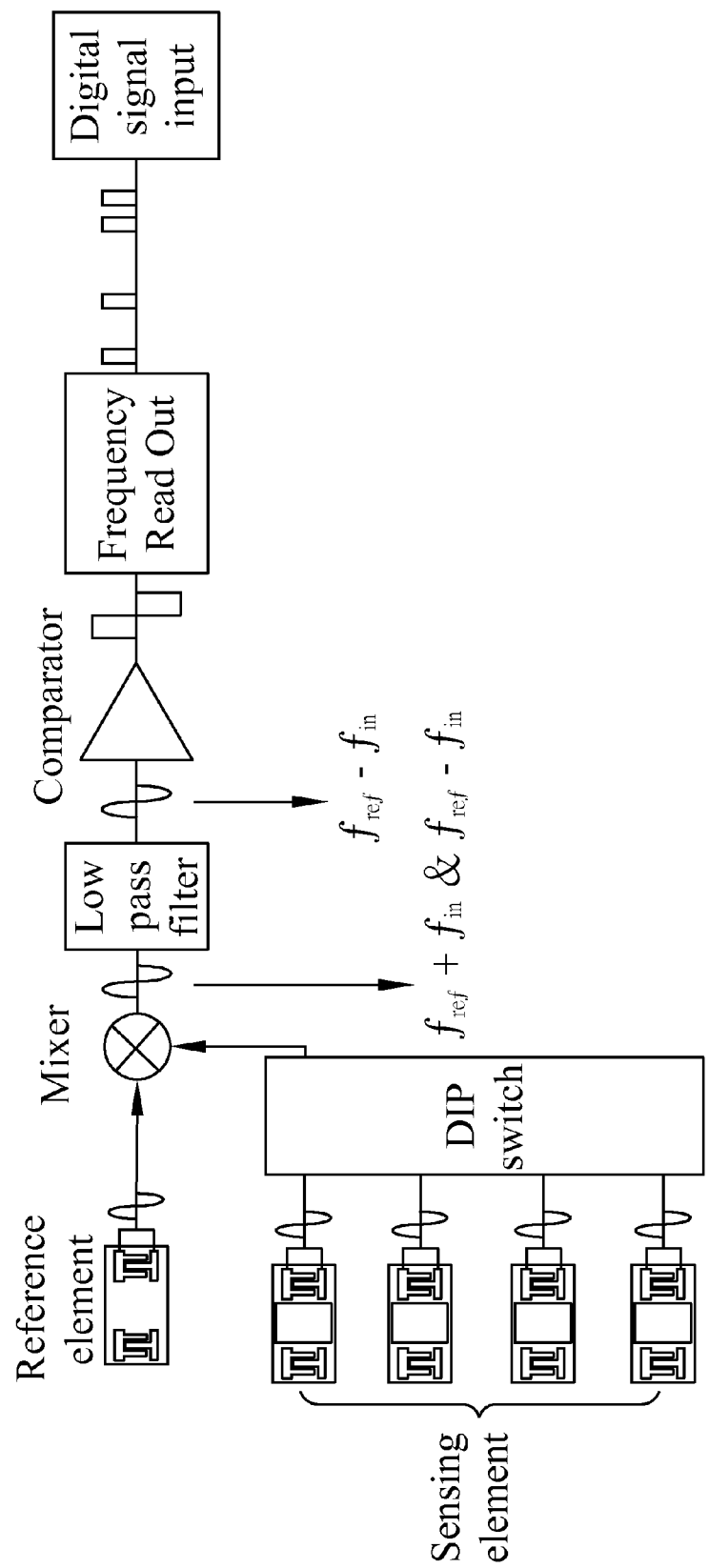
FIG. 4B is a block diagram of a surface acoustic wave sensor interface circuit of a gas recognition chip in accordance with a preferred embodiment of the present invention.

With reference to FIGS. 4A and 4B for a circuit diagram of an adjustable oscillator circuit of a surface acoustic wave sensor interface circuit of a gas recognition chip in accordance with a preferred embodiment of the present invention and a block diagram of a surface acoustic wave sensor interface circuit of a gas recognition chip in accordance with a preferred embodiment of the present invention respectively the sensor array 131 includes surface acoustic wave (SAW) sensors. Since an oscillator circuit of the general surface acoustic wave sensor is designed with a specific frequency, its usage has lots of limitations. The present invention provides an adjustable oscillator circuit. The adjustable oscillator circuit adjusts the oscillation frequency by different surface acoustic wave sensors to improve the flexibility of its usage. FIG. 4A shows an adjustable high-frequency oscillator circuit with a positive feedback oscillation mode.

FIG. 4B is a block diagram illustrating a preferred embodiment of the surface acoustic wave sensor interface circuit. Preferably, each surface acoustic wave unit includes two surface acoustic wave elements for eliminate the effect of environment factors such as pressure, temperature and humidity on the surface acoustic wave sensor based on the principle of differential circuit. In the figure, each surface acoustic wave sensing unit comprises two surface acoustic wave elements: one is a sensing element selected by a dual in-line package (DIP) switch, and the other one is a reference element. Each surface acoustic wave element has a corresponding oscillator circuit. The aforementioned two elements are processed by a mixer to generate signals $f_{ref}+f_{in}$ and $f_{ref}-f_{in}$ with different frequencies. After the signals are passed through a low-pass filter (LPF), only the signal $f_{ref}-f_{in}$ (which is the part with a changed frequency) is outputted. This signal is passed through a comparator to produce a square wave, and a digital logic gate of a Frequency Read Out is used to output the signal with a changed frequency for further processing, so as to achieve the low power consumption and the better frequency resolution.

Figure 5:
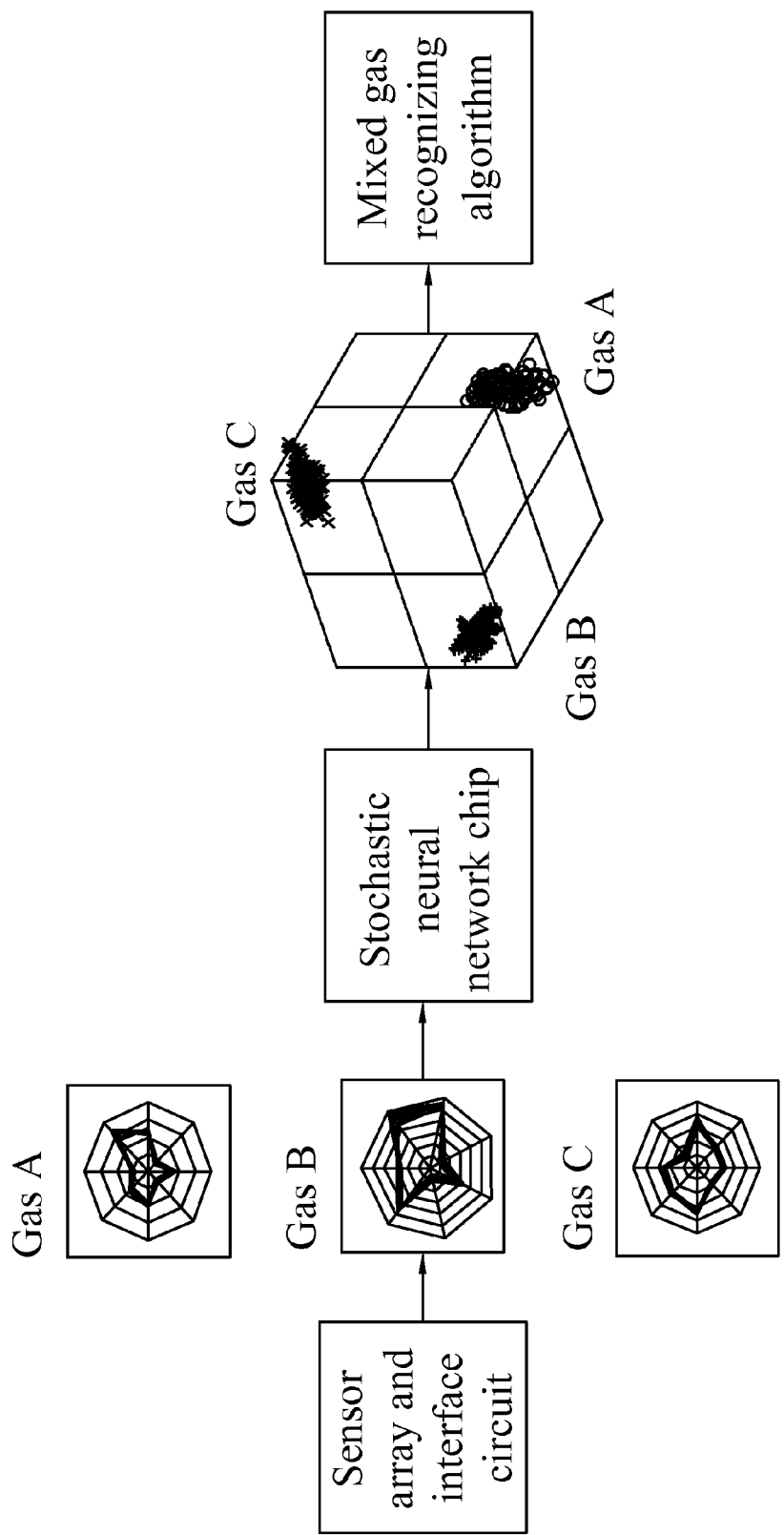
FIG. 5 is a schematic view of a stochastic neural network chip of a gas recognition chip in accordance with the present invention.

With reference to FIG. 5 for a schematic view of a stochastic neural network chip of a gas recognition chip in accordance with the present invention, the stochastic neural network chip is integrated into the gas recognizing device of the medical ventilator. The stochastic neural network chip can reduce the dimensions of the gas pattern signal of the sensor and amplify the differential between different types of gases. Finally, the mixed gas recognizing algorithm is executed, so that the gas recognizing device can recognize the complicated compositions of the mixed gas in the ward of a hospital. Preferably, the stochastic neural network chip can integrate a continuous restricted Boltzmann machine (CRBM) which is implemented as a modular analog chip system. An article by Lu, C.C. and Chen, H., "Current-mode Computation with Noise in a Scalable and Programmable Probabilistic Neural VLSI System" has been published. Therefore, the present invention adopts the stochastic neural network chip based on the continuous restricted Boltzmann machine and integrated into a gas recognition chip of a medical ventilator, so that the gas recognition chip can process biomedical signals with many noises and large variance. The continuous restricted Boltzmann machine used for the pretreatment of the gas signal can amplify the difference of different types of signals stably, and learn the main characteristic of the signal distribution to obtain an output with dimension smaller than that of the original signal. The computation of the back-end processor can be reduced effectively. In addition, the continuous restricted Boltzmann machine has a learning ability capable of timely and appropriately adjusting the model parameters to maintain reliable recognition ability for the different sensors, different gas compositions, or the shift of the sensor resulted from a long time of usage.

Figure 6A:
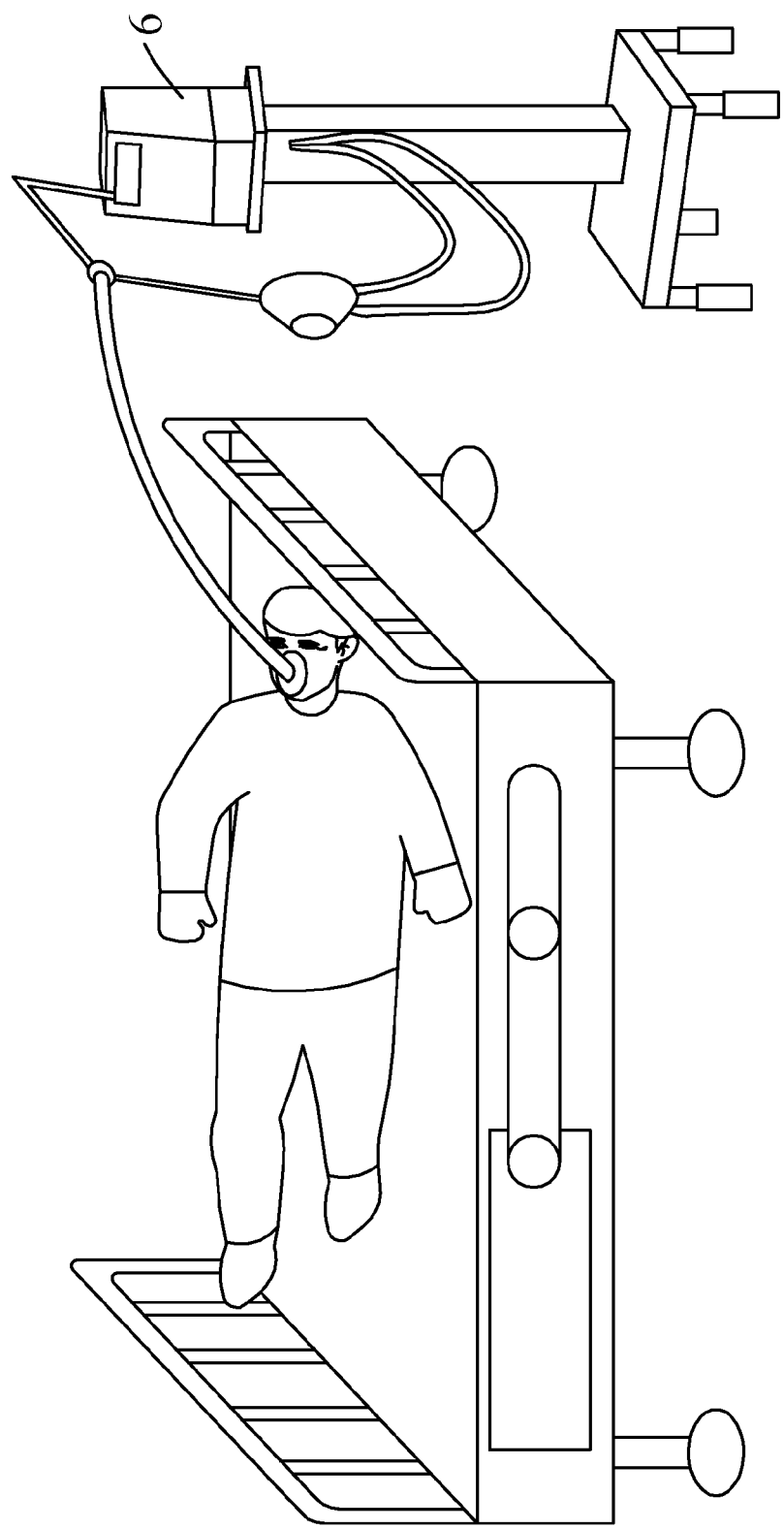
FIGS. 6A, 6B and 6C are schematic views showing practical application of a medical ventilator capable of early detecting and recognizing types of pneumonia in accordance with the present invention.
Figure 6B:
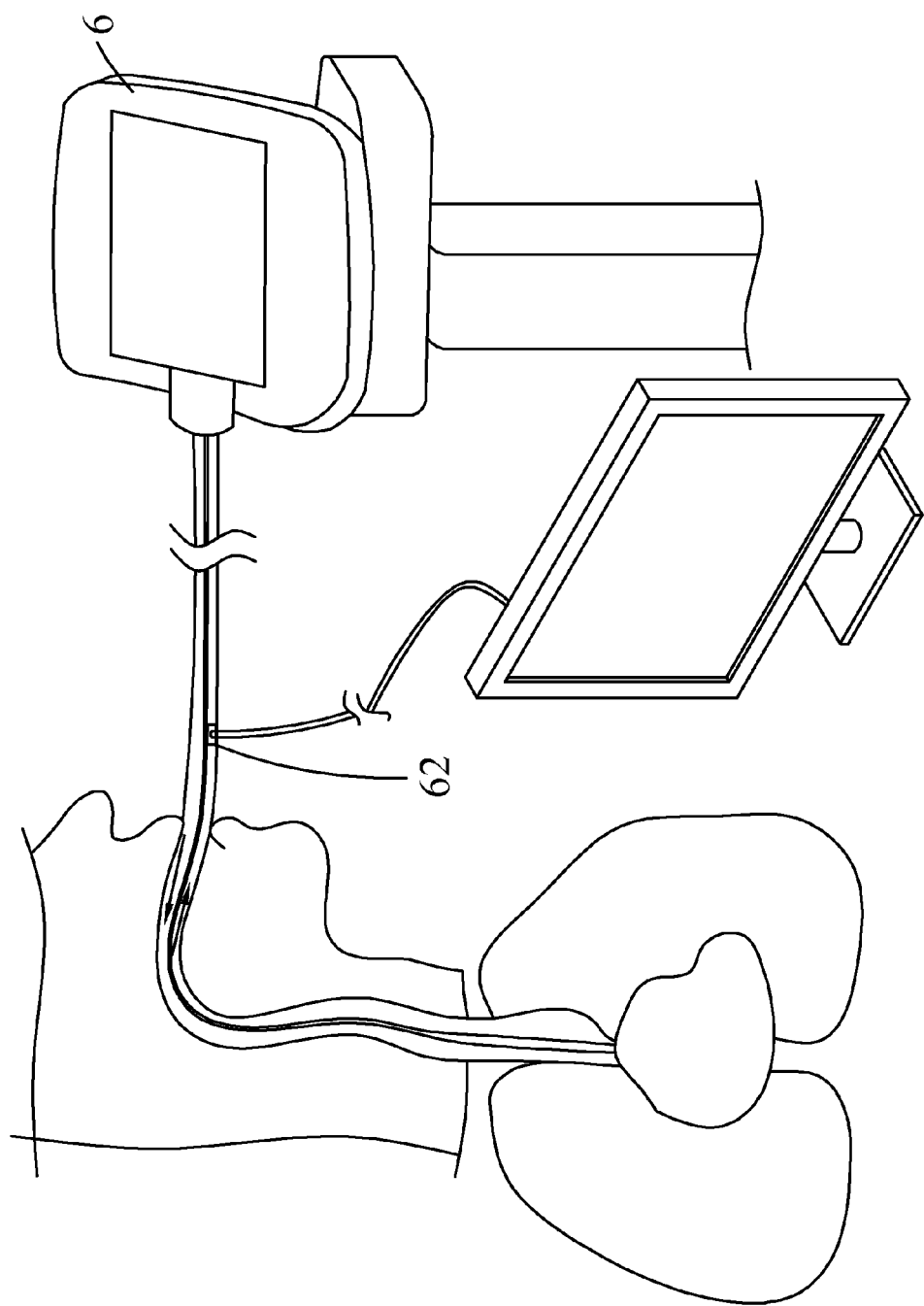
Figure 6C:
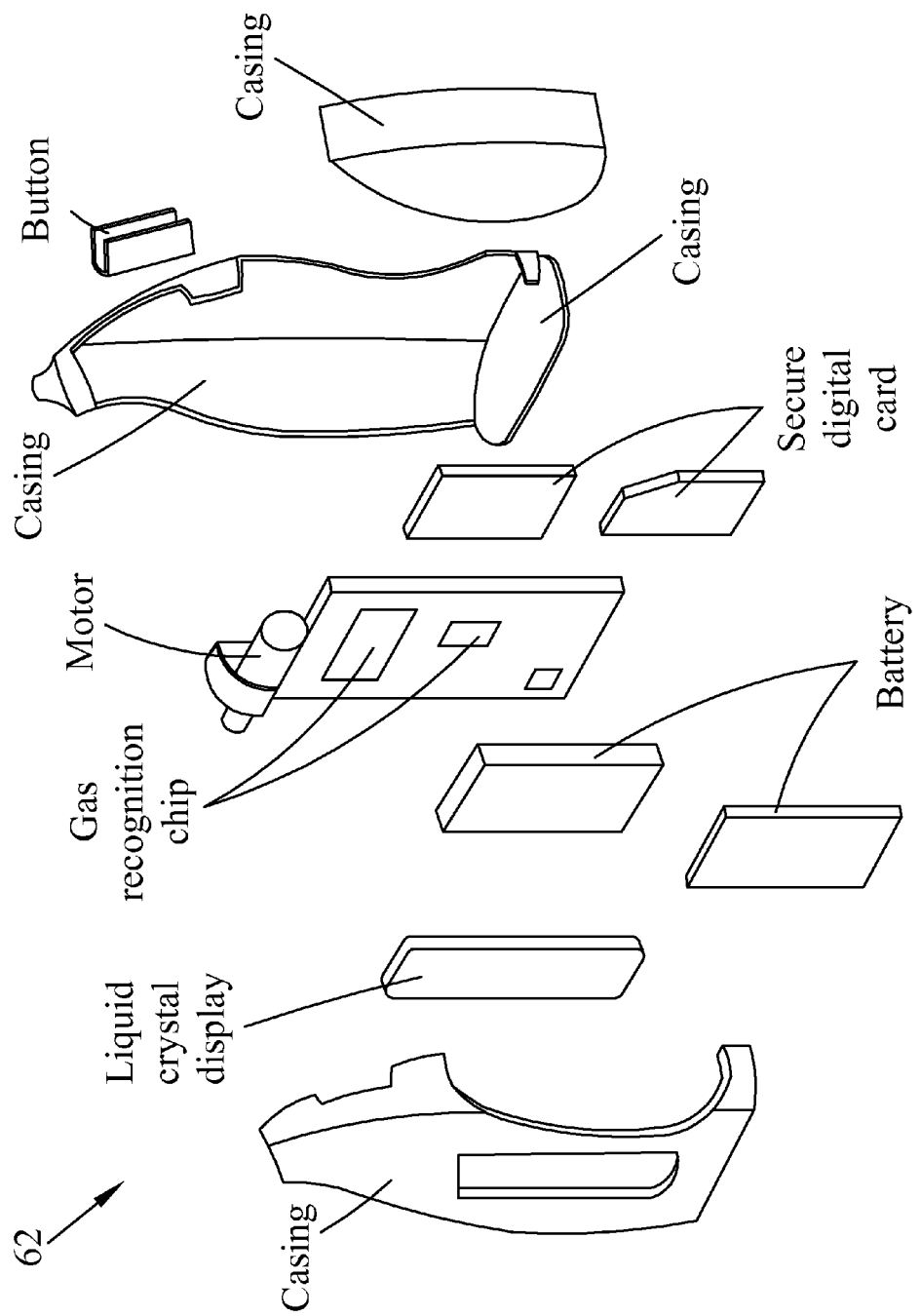

With reference to FIGS. 6A, 6B and 6C, which are schematic views of practical applications of the medical ventilator capable of early detecting and recognizing types of pneumonia in accordance with a preferred embodiment of the present invention. FIG. 6A shows that a patient in an intensive care unit uses a medical ventilator 6 capable of early detecting and recognizing types of pneumonia in accordance with the present invention for detection. FIG. 6B shows that a doctor finds that a patient is infected by pneumonia, uses a gas recognizing device 62 integrated into a medical ventilator to analyze a gas aspired by the patient, determine the type of pneumonia of infecting the patient, and provides a medical treatment immediately. In FIG. 6B, the gas recognizing device 62 can be set inside the aspiration pipeline or connected to an aspiration pipeline outside the patient to capture the gas aspired by the patient for the recognition. The gas recognition system is executed with a system-on-a-chip (SoC), so that a portable electronic device with low voltage, low power and a recognition function can be achieved as shown in FIG. 6C. On the other hand, the present invention further integrates the gas recognition system into the medical ventilator to assist doctors to made immediate diagnosis for a patient infected by pneumonia. Obviously, the present invention improves over the prior art. Preferably, the gas recognizing device 62 is connected directly to the aspiration pipeline outside the body of the patient in order to capture the gas aspired by the patient to identify the gas.

Further, the gas recognition chip of the present invention further detects various different gases. For example, the gas recognition chip can be used for detecting the freshness of seafood, determining whether a liquid is a fake liquor, detecting whether clothes or furniture contain harmful chemicals, inspecting whether a public space contains harmful gases, or searching for dead bodies of victims after a natural disaster. Obviously, the present invention meets the requirements of industrial applications.

Even though the concept of the method for recognizing gas by a medical ventilator capable of early detecting and recognizing the types of pneumonia in accordance with the present invention has been described in the section of the medical ventilator of the present invention already, the following flow chart is provided for illustrating the invention more clearly.

Figure 7:
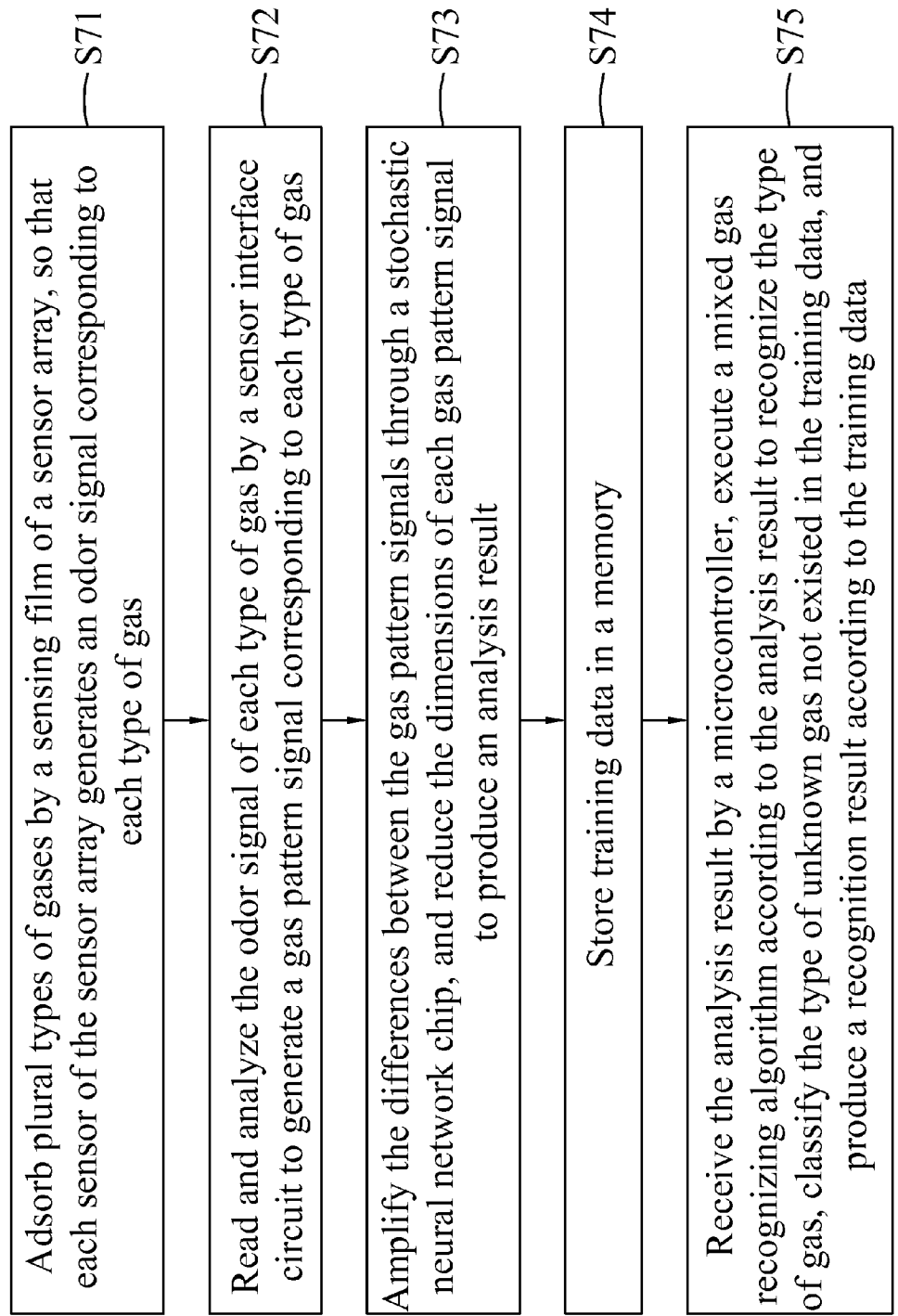
FIG. 7 is a flow chart of a method for recognizing gas of a medical ventilator capable of early detecting and recognizing types of pneumonia in accordance with the present invention.

With reference to FIG. 7 for a flow chart of a method for recognizing gas of a medical ventilator capable of early detecting and recognizing types of pneumonia in accordance with the present invention, the method comprises the following steps:

S71: Adsorb plural types of gases by a sensing film of a sensor array, so that each sensor of the sensor array generates an odor signal corresponding to each type of gas.

S72: Read and analyze the odor signal of each type of gas by a sensor interface circuit to generate a gas pattern signal corresponding to each type of gas.

S73: Amplify the differences between the gas pattern signals through a stochastic neural network chip, and reduce the dimensions of each gas pattern signal to produce an analysis result.

S74: Store training data in a memory.

S75: Receive the analysis result by a microcontroller, execute a mixed gas recognizing algorithm according to the analysis result to recognize the type of gas, classify the type of unknown gas not existed in the training data, and produce a recognition result according to the training data.

The details and implementation of the method for recognizing gas by a medical ventilator capable of early detecting and recognizing the types of pneumonia have been described in the section of the medial ventilator already, and thus will not be repeated.

In summation of the description above, the present invention adopts a stochastic neural network chip for the pretreatment of the gas pattern signal, so as to achieve the effects of reducing the computation and power of the system and improve the recognition precision significantly. In addition, the present invention adopts an algorithm with robustness and adaption to recognize a mixed gas and classify an unknown gas effectively, not only capable of recognizing the unknown gas accurately, but also capable of classifying the gas, so that the system of the present invention can have a self-learning ability. In addition, the gas recognition system can be executed with a system-on-a-chip to reduce the volume of the gas recognizing device significantly and integrated with the medical ventilator. The present invention not only can assist doctors to make correct diagnosis of the types of pneumonia of each patient, but also can be integrated with other portable electronic devices to execute different functions.

In summation of the description above, the present invention breaks through the prior, achieves the expected effects, and complies with the patent application requirements, and thus is duly filed for patent application. While the invention has been described by means of specific embodiments, numerous modifications and variations could be made thereto by those skilled in the art without departing from the scope and spirit of the invention set forth in the claims.

What is claimed is:

1. A gas recognition chip, comprising:
    a sensor array, including a plurality of sensors and a plurality of sensing films applied on the sensors correspondingly, and each of the sensing films being provided with selectivity to adsorb plural types of gases, and each of the sensors being provided to produce an odor signal corresponding to each of the respective gases adsorbed by the sensing film;
    a sensor interface circuit, for reading and analyzing the odor signal of each of the gases to generate a gas pattern signal corresponding to each of the respective gases;
    a stochastic neural network chip, for amplifying the difference between the gas pattern signals and reducing the dimensions of each gas pattern signal to produce an analysis result;
    a memory, for storing gas training data; and
    a microcontroller, for receiving the analysis result, and executing a mixed gas recognizing algorithm according to the analysis result to recognize the type of the gas, and classify an unknown gas not existed in the gas training data, and producing a recognition result according to the gas training data,
    wherein the microcontroller transmits data of the unknown gas to the stochastic neural network chip and the memory when the microcontroller detects the unknown gas, so that the gas recognition chip has a self learning ability,
    wherein the mixed gas recognizing algorithm includes a K nearest neighbor (KNN) algorithm, a linear least squares regression algorithm and a median-threshold K nearest neighbor (MTKNN) classification algorithm, and the median-threshold K nearest neighbor classification algorithm is used to find a distance between every two data in the gas training data first, and then find a median of the distances to determine whether the gas is the unknown gas.

2. The gas recognition chip of claim 1, wherein the sensing film is made of a nanoporous carbon material and provided for growing a polymer with gas adsorbability in pores of the nanoporous carbon material.

3. The gas recognition chip of claim 1, wherein the sensor array is comprised of conducting polymer (CP) sensors.

4. The gas recognition chip of claim 3, wherein the sensor interface circuit stores electric charges by a single polysilicon floating gate element to reduce electric leakage and circuit power.

5. The gas recognition chip of claim 1, wherein the sensor array is comprised of surface acoustic wave (SAW) sensors.

6. The gas recognition chip of claim 5, wherein the sensor interface circuit includes an adjustable oscillator circuit capable of adjusting an oscillation frequency according to different surface acoustic wave sensors to enhance the flexibility of usage.

7. A medical ventilator capable of early detecting and recognizing types of pneumonia, comprising an aspiration pipeline and a gas recognizing device, wherein the gas recognizing device uses a gas recognition chip to analyze a gas aspired by a patient from the aspiration pipeline to identify the type of pneumonia, the gas recognition chip is the one recited in the claim 1.

8. The medical ventilator capable of early detecting and recognizing types of pneumonia as recited in claim 1, wherein the gas recognizing device is coupled directly to the aspiration pipeline outside the patient's body, and the gas aspired by the patient is collected to perform a recognition.

9. A method for recognizing gas, comprising the steps of:
    providing a sensor array, including a plurality of sensors and a plurality of sensing films applied on the sensors correspondingly;
    using each of the sensing films with selectivity to adsorb plural types of gases, and using each of the sensors to generate an odor signal corresponding to each of the respective gases adsorbed by the sensing film;
    using a sensor interface circuit to read and analyze the odor signal of each of the gases to generate a gas pattern signal corresponding to each of the respective gases;
    using a stochastic neural network chip to amplify the difference between the gas pattern signals and reduce the dimensions of each of the gas pattern signals to produce an analysis result;
    storing gas training data in a memory; and
    using a microcontroller to receive the analysis result, and execute a mixed gas recognizing algorithm to identify the type of the gas according to the analysis result, and classify an unknown gas not existing in the gas training data, and then produce a recognition result according to the gas training data,
    wherein when the unknown gas is detected, the data of the unknown gas is transmitted to the stochastic neural network chip and the memory by the microcontroller, so that the gas recognition chip has a self-learning ability,
    wherein the mixed gas recognizing algorithm includes a K nearest neighbor algorithm, a linear least squares regression algorithm and a median-threshold K nearest neighbor classification algorithm, wherein the median-threshold K nearest neighbor classification algorithm is used to find a distance between every two data in the gas training data, and then find a median of the distances, and the median is used to determine whether the gas is the unknown gas.

10. The method for recognizing gas as recited in claim 9, wherein the sensing film is made of a nanoporous carbon material and a polymer with gas adsorbability is grown in pores of the nanoporous carbon material.

11. The method for recognizing gas as recited in claim 9, wherein the sensor array is comprised of conducting polymer sensors.

12. The method for recognizing gas as recited in claim 11, wherein the sensor interface circuit stores electric charges by a single polysilicon floating gate element to reduce electric leakage and circuit power.

13. The method for recognizing gas as recited in claim 9, wherein the sensor array is comprised of surface acoustic wave sensors.

14. The method for recognizing gas as recited in claim 13, wherein the sensor interface circuit includes an adjustable oscillator circuit for adjusting an oscillation frequency according to different surface acoustic wave sensors to enhance the flexibility of usage.

* * * * *